United States Patent
Kawasaki et al.

(10) Patent No.: US 11,142,742 B2
(45) Date of Patent: Oct. 12, 2021

(54) INCUBATOR

(71) Applicant: AIREX CO., LTD., Nagoya (JP)

(72) Inventors: Koji Kawasaki, Nagoya (JP); Hideo Nishiwaki, Nagoya (JP); Daisuke Kakuda, Nagoya (JP); Jun Masudome, Nagoya (JP); Yukihiro Yazaki, Nagoya (JP); Zhiqiang Guo, Nagoya (JP); Tsukasa Kitano, Nagoya (JP)

(73) Assignee: AIREX CO., LTD.

( * ) Notice: Subject to any disclaimer, the term of this patent is extended or adjusted under 35 U.S.C. 154(b) by 48 days.

(21) Appl. No.: 16/613,038

(22) PCT Filed: May 9, 2018

(86) PCT No.: PCT/JP2018/017881
§ 371 (c)(1),
(2) Date: Nov. 12, 2019

(87) PCT Pub. No.: WO2018/212029
PCT Pub. Date: Nov. 22, 2018

(65) Prior Publication Data
US 2020/0199518 A1 Jun. 25, 2020

(30) Foreign Application Priority Data
May 15, 2017 (JP) .............................. JP2017-096398

(51) Int. Cl.
*C12M 1/00* (2006.01)
*C12M 1/12* (2006.01)
*C12M 1/34* (2006.01)

(52) U.S. Cl.
CPC ............ *C12M 41/14* (2013.01); *C12M 23/06* (2013.01); *C12M 29/24* (2013.01); *C12M 41/40* (2013.01); *C12M 41/44* (2013.01)

(58) Field of Classification Search
CPC ..................................................... C12M 41/14
See application file for complete search history.

(56) References Cited

U.S. PATENT DOCUMENTS

| 4,336,329 A * | 6/1982 | Hesse ................. C12M 41/14 |
| | | 422/298 |
| 2014/0238496 A1* | 8/2014 | Offner ................ C12M 29/26 |
| | | 137/1 |

FOREIGN PATENT DOCUMENTS

| JP | 05-059426 A | 3/1993 |
| JP | 2010-124703 A | 6/2010 |

(Continued)

*Primary Examiner* — Jonathan M Hurst
(74) *Attorney, Agent, or Firm* — Yakov Sidorin; Quarles & Brady LLP

(57) ABSTRACT

An incubator which can uniformly maintain a temperature/ humidity in a culture chamber and prevent dew condensation from occurring in the culture chamber is provided. Further, an incubator which raises an air pressure in a culture chamber higher than that of the external environment to maintain an aseptic environment and prevents water vapor to be supplied from adversely affecting the inner aseptic environment is provided.

An incubator includes a culture chamber including an insulated door and insulated wall, circulating means for circulating air in the culture chamber, temperature regulating means for regulating a temperature of the air in the culture chamber, and humidifying means for humidifying the air in the culture chamber. The humidifying means includes compressed gas generating means for generating a compressed gas, water supplying means for supplying water, a mixed gas-liquid regulator which regulates a mixed gas-liquid having compressed air and the water mixed therein, and a vaporizer which vaporizes the mixed gas-liquid to produce water vapor. Furthermore, the water vapor produced by the (Continued)

vaporizer can be directly supplied to the air circulated by the circulating means without passing through an air filter.

7 Claims, 5 Drawing Sheets

(56) References Cited

FOREIGN PATENT DOCUMENTS

| | | |
|---|---|---|
| JP | 2011-002150 A | 1/2011 |
| JP | 2017-077208 A | 4/2017 |
| WO | 2015/166554 A1 | 11/2015 |

* cited by examiner

INCUBATOR

CROSS-REFERENCE TO RELATED APPLICATIONS

This patent application represents the U.S. national stage entry of International Application No. PCT/JP2018/017881, filed on May 9, 2018, and claims priority from Japanese Patent Application No. 2017-096398, filed on May 15, 2017, the disclosures of which are incorporated by reference herein.

TECHNICAL FIELD

The present invention relates to an incubator, and more particularly to an incubator which has characteristics in humidifies in particular, adequately controls a temperature/humidity appropriate for incubation, and can maintain an aseptic environment in a culture chamber at a high level.

BACKGROUND ART

With the development of a regenerative medicine field in recent years, cells are extensively cultured with the use of an incubator. To culture cells, a culture environment suitable for each cell must be maintained, and a temperature condition and a humidity condition, or carbon dioxide concentration, nitride gas concentration, and others as required in the incubator are adjusted.

To adjust the temperature condition in the incubator, a hot water heater or an electric heater is generally incorporated in a wall portion, e.g., the interior, a door, or a shelf board of the incubator, and an indoor temperature is adjusted by radiant heat from a wall surface. Further, to adjust the humidity condition in the incubator, a humidification pan is generally provided in the incubator to store water, and the indoor humidity is adjusted by natural evaporation of this stored water. On the other hand, to adjust the carbon dioxide concentration or the nitrogen gas concentration in the incubator, a carbon dioxide concentration sensor or a nitrogen gas concentration sensor and a supply path from a carbon dioxide cylinder or a nitrogen gas cylinder are provided, and the carbon dioxide concentration or the nitrogen gas concentration is thereby adjusted. Furthermore, in addition to these adjustments, stirring of air using an indoor fan is also adopted to achieve uniformization in some cases.

However, the indoor temperature adjustment and the indoor humidity adjustment based on the radiant heat from the wall surface or the stirring of air are apt to lead to non-uniformity of the temperature/humidity. In particular, since the humidity is high in the incubator, there is a problem that partial dew condensation is likely to occur when the temperature/humidity is non-uniform.

On the other hand, conventional incubators cannot guarantee the grade A (production guide lines for sterile pharmaceutical products by Health, Labor and Welfare Ministry) conforming to GMP (Good Manufacturing Practice). Moreover, even if the inside of each of such incubators is sterilized to the grade A, an air pressure cannot be maintained higher than that of the external environment to keep this grade. Additionally, water is supplied from the outside in association with evaporation of the stored water in the incubator, but there occurs a problem that the water supplied from the outside adversely affects the interior aseptic environment in this case.

Thus, in an incubator according to the following Patent Literature 1, there is suggested that general temperature adjustment is performed by turning on/off an indoor heater, a door heater, and a stage heater and an area of a water surface exposed in a humidification pan is finely adjusted when the inside humidity has risen and dew condensation has become apt to occur so that an accuracy of humidity adjustment can be improved. Further, in an incubator according to the following Patent Literature 2, providing a filter in a water feed path from the outside of the incubator to a humidification pan is suggested.

CITATION LIST

Patent Literatures

Patent Literature 1: Japanese Unexamined Patent Application Publication No. 2008-005759
Patent Literature 2: Japanese Unexamined Patent Application Publication No. 2011-160672

SUMMARY OF INVENTION

Problem to be Solved by the Invention

Meanwhile, in the incubator according to the above Patent Literature 1, the occurrence of dew concentration can be reduced, but there is a problem that the indoor temperature/humidity is apt to become non-uniform. Furthermore, in the incubator according to the above Patent Literature 2, sterilization of the water stored in the humidification pan can be assured, but there is a problem that the indoor temperature/humidity is likewise apt to become non-uniform.

Therefore, it is an object of the present invention to provide an incubator which can cope with the above-described various problems and uniformly maintain a temperature/humidity in a culture chamber without producing dew condensation in the culture chamber. Moreover, it is an object of the present invention to provide an incubator which increases an air pressure in a culture chamber higher than that of the external environment to maintain an aseptic environment and prevents water vapor to be supplied from adversely affecting the inner aseptic environment.

Means for Solving Problems

To solve the problems, as a result of the keen studies, the present inventors have found that circulating air in a culture chamber and appropriately supplying a small amount of sterilized water vapor to a circulation path can prevent an adverse effect on an aseptic environment in the culture chamber and can uniformly maintain a temperature/humidity in the culture chamber, thus bringing the present invention to completion.

That is, according to the description of claim 1, an incubator of the present invention includes: a culture chamber (20) which includes an insulated door (20a) and insulated walls (20b, 20c 20d); circulating means (30) for circulating air in the culture chamber; temperature regulating means (40) for regulating a temperature of the air in the culture chamber; and humidifying means (50) for humidifying the air in the culture chamber, the humidifying means includes: compressed gas generating means (51) for generating a compressed gas; water supplying means (52) for supplying water; a mixed gas-liquid regulator (53) which regulates a mixed gas-liquid having the compressed air and the water mixed therein; and a vaporizer (54, 55) which vaporizes the mixed gas-liquid to produce water vapor, and the water vapor produced by the vaporizer is directly supplied to the air circulated by the circulating means without passing through an air filter.

Further, according to the description of claim 2, the present invention is the incubator set forth in claim 1, and characterized by including air supplying means (21) and exhausting means (37) which can maintain higher air pressure in the incubator than that of the external environment.

Furthermore, according to the description of claim 3, the present invention is the incubator set forth in claim 1 or 2, and characterized in that the circulating means includes: a circulation path (32) including a circulation fan (31) configured to supply the air sucked from one end portion of the culture chamber into the culture chamber through the other end portion of the same; and a rectifying member (34) which rectifies the air supplied into the culture chamber through the circulating path, and the air supplied into the culture chamber through the circulation path and the rectifying member forms air of a unidirectional flow which substantially horizontally flows in the culture chamber.

Moreover, according to the description of claim 4, the present invention is the incubator set forth in any one of claims 1 to 3, and characterized in that the compressed gas is a mixed gas containing one or more of respective gases which are air, carbon dioxide, and nitrogen.

Additionally, according to the description of claim 5, the present invention is the incubator set forth in any one of claims 1 to 4, and characterized in that a supply amount of the water vapor discharged by the vaporizer falls within the range of 1 g/hr. to 60 g/hr.

Further, according to the description of claim 6, the present invention is the incubator set forth in any one of claims 1 to 5, and characterized in that the vaporizer (54) includes an outer cylindrical tube (61) having a cylindrical shape and a heating element (62) incorporated in the outer cylindrical tube in parallel with a longitudinal direction thereof, and the water vapor heated and sterilized while the mixed gas-liquid passes through a space between the outer cylindrical tube and the heating element is supplied.

Furthermore, according to the description of claim 7, the present invention is the incubator set forth in claim 6, and characterized in that the heating element has a heater (63) coated with quartz glass (64).

Moreover, according to the description of claim 8, the present invention is the incubator set forth in any one of claims 1 to 5, and characterized in that the vaporizer (55) includes an outer cylindrical tube (71) having a cylindrical shape and a heating element (72) incorporated in the outer cylindrical tube in parallel with a longitudinal direction thereof, the heating element includes a rod-like heater (73) arranged in a longitudinal direction thereof and an evaporator tube (74) spirally wound around an outer periphery of the heater in the longitudinal direction, and the water vapor heated and sterilized while the mixed gas-liquid passes through the evaporator tube is supplied.

Effect of the Invention

According to the above-described configuration, the incubator of the present invention has the culture chamber, the circulating means, the temperature regulating means, and the humidifying means. The culture chamber includes the insulated door and the insulated walls. The circulating means circulates air in the culture chamber. The temperature regulating means regulates a temperature of the air in the culture chamber. The humidifying means humidifies the air in the culture chamber.

Additionally, the humidifying means includes the compressed gas generating means, the water supplying means, the mixed gas-liquid regulator, and the vaporizer. The mixed gas-liquid regulator mixes a compressed gas generated by the compressed gas generating means with water supplied from the water supplying means to produce a mixed gas-liquid. The vaporizer vaporizes the produced mixed gas-liquid to generate water vapor. The water vapor generated by the vaporizer in this manner is directly supplied to the air circulated by the circulating means without passing through an air filter. Consequently, the temperature/humidity in the culture chamber can be uniformly maintained, and dew condensation is not produced in the culture chamber. Further, the water vapor generated by the vaporizer does not adversely affect the inner aseptic environment.

Furthermore, according to the above-described configuration, the incubator of the present invention has the air supplying means and the exhausting means. The air supplying means supplies air in the external environment to the inside of the culture chamber. On the other hand, the exhausting means exhausts the air in the culture chamber to the exterior environment. Functions of the air supplying means and the exhausting means enable maintaining a higher air pressure in the culture chamber than in the external environment. Consequently, the inside of the culture chamber has a positive pressure higher than that in the external environment, and the aseptic environment can be maintained at a high level without being contaminated by the external environment.

Moreover, according to the above-described configuration, the circulating means includes the circulation path and the rectifying member. The circulation path has the circulation fan configured to supply the air sucked from one end portion of the culture chamber to the inside of the culture chamber through the other end portion of the same. The rectifying member rectifies the air supplied into the culture chamber through the circulation path. In this manner, the air in the culture chamber circulates in the culture chamber by an operation of the circulation fan. During this circulation, the air in the culture chamber is regulated to a predetermined temperature by the temperature regulating means and humidified by the humidifying means. The heated and humidified air forms air of a unidirectional flow (which is a so-called laminar flow) which substantially horizontally flows in the culture chamber through the circulation path and the rectifying member by the operation of the circulation fan.

Consequently, the air having the set temperature/set humidity is constantly supplied to each petri dish filled with a preparation set in the culture chamber. Thus, the temperature/humidity in the culture chamber can be uniformly maintained, and the dew condensation does not occur in the culture chamber. Further, since the air having the uniform temperature/humidity flows in the culture chamber as the unidirectional flow, a temperature in the petri dish filled with an object to be cultured can be increased to a predetermined temperature in a short time as different from temperature rising based on the radiant heat or the stirring of air.

Furthermore, according to the above-described configuration, a compressed gas generated by the compressed gas generating means is a mixed gas containing one or more of respective gases which are air, carbon dioxide, and nitrogen. Thus, the water vapor can be generated by the vaporizer, and the concentration of the air, the carbon dioxide, or the nitrogen required for the culture environment can be uniformly maintained in a predetermined range.

Moreover, according to the above-described configuration, a supply amount of the water vapor discharged by the vaporizer falls within the range of 1 g/hr. to 60 g/hr. Thus, since an extremely small amount of the water vapor can be supplied stably or as required, the temperature/humidity in the culture chamber can be uniformly maintained, and the dew condensation does not occur in the culture chamber.

Additionally, according to the above-described configuration, the vaporizer includes an outer cylindrical tube having a cylindrical shape and a heating element. This heating element is incorporated in the outer cylindrical tube in parallel with a longitudinal direction of the outer cylindrical tube. Consequently, the mixed gas-liquid produced in the mixed gas-liquid regulator is heated while passing through a space between the outer cylindrical tube and the heating element and supplied into the culture chamber as the sterilized water vapor. In this manner, since the water vapor produced by the vaporizer is sterilized at a high temperature, it is directly supplied into the culture chamber without passing through an air filter.

Further, according to the above-described configuration, the heating element provided in the vaporizer may have a heater covered with quartz glass. Consequently, the water vapor produced by the vaporizer is not contaminated, and the aseptic environment as well as a dustless environment in the culture chamber can be maintained at a high level.

Furthermore, according to the above-described configuration, the heating element provided in the vaporizer may include a rod-like heater arranged in the longitudinal direction thereof and an evaporator tube spirally wound around an outer periphery of the heater along the longitudinal direction. Consequently, the mixed gas-liquid produced by the mixed gas-liquid regulator is heated while passing through the evaporator tube and supplied into the culture chamber as the sterilized water vapor. In this manner, the water vapor produced by the vaporizer is sterilized at a high temperature, and hence it is directly supplied into the culture chamber without passing through the air filter.

As described above, according to the present invention, it is possible to provide the incubator which can uniformly maintain the temperature/humidity in the culture chamber without producing the dew condensation in the culture chamber. Moreover, according to the present invention, it is possible to provide the incubator which maintains the aseptic environment by increasing an air pressure in the culture chamber higher than that in the external environment and prevents the water vapor to be supplied from adversely affecting the inner aseptic environment.

It is to be noted that a sign in parenthesis of each means mentioned above denotes a correspondence relationship with specific means described in the following embodiment.

BEST MODE(S) FOR CARRYING OUT THE INVENTION

Figure 1:
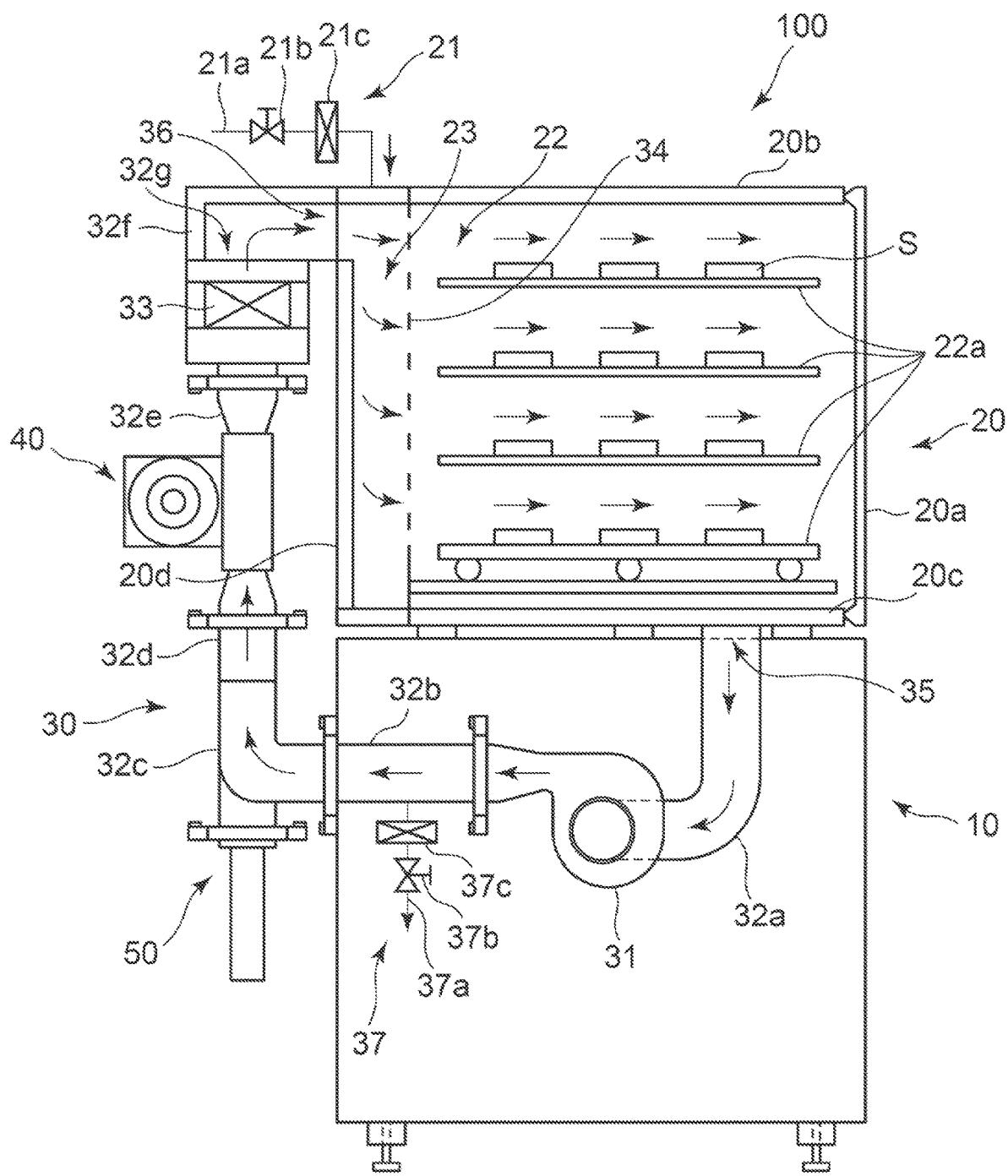
FIG. 1 is a cross-sectional view showing the inside an embodiment of an incubator according to the present invention from a side surface.
Figure 2:
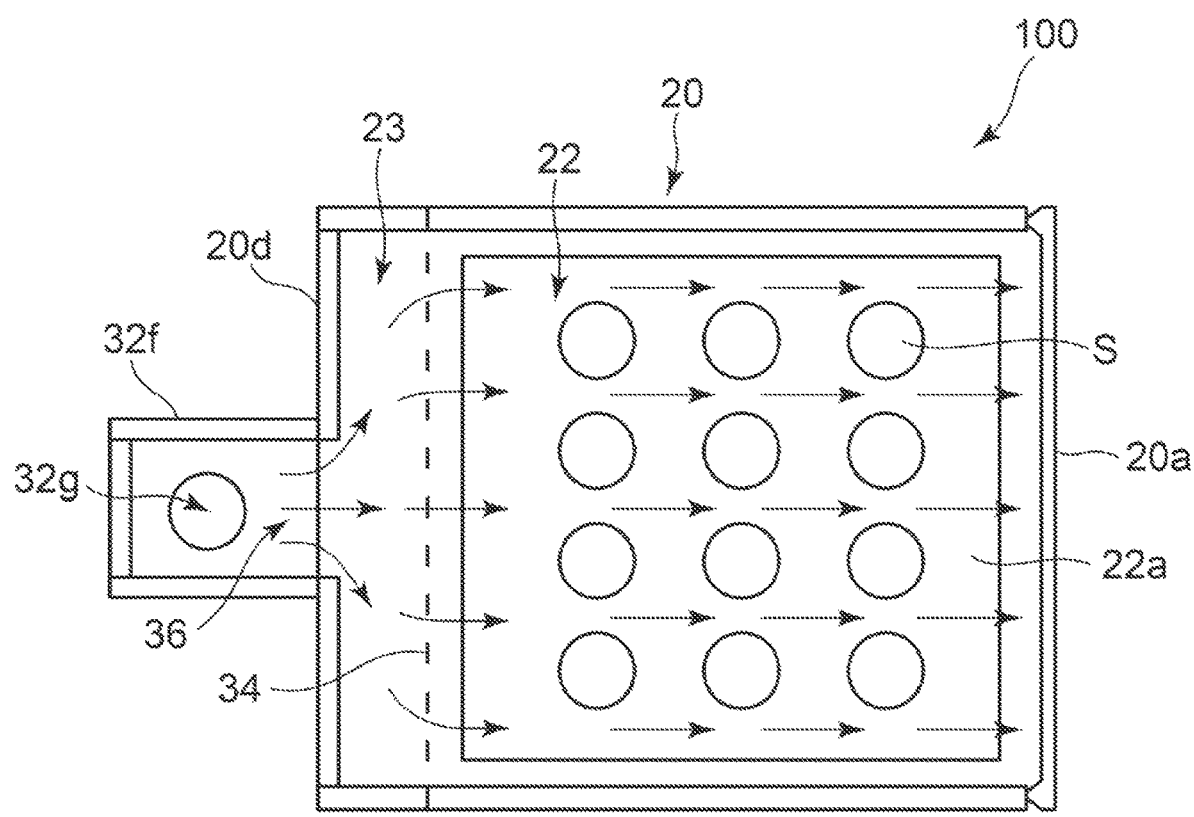
FIG. 2 is a cross-sectional view showing the inside of the incubator shown in FIG. 1 from an upper surface.

An embodiment of an incubator according to the present invention will now be described hereinafter with reference to the drawings. FIG. 1 is a cross-sectional view showing the inside of an embodiment of the incubator according to the present invention from a side surface. Further, FIG. 2 is a cross-sectional view showing the inside of this incubator from an upper surface. In FIG. 1 and FIG. 2, the incubator 100 is constituted of a base 10 mounted on a floor surface, a culture chamber 20 placed on this base 10, a circulation device 30 which circulates air in this culture chamber 20, a temperature regulating device 40 which regulates a temperature of the air in the culture chamber 20, and a humidifying device 50 which humidifies the air in the culture chamber.

An outer wall and an inner wall of the culture chamber 20 are covered with a metal plate made of stainless steel, and a space between the outer wall and the inner wall is filled with a heat insulating material to form an insulated wall. It is to be noted that a heater which heats the inside of the culture chamber 20 may be incorporated in the insulated wall. Furthermore, a front wall portion of the culture chamber 20 is an openable/closeable insulated door 20a, and airtight shieling from the external environment is effected and an interior aseptic environment (e.g., the grade A) can be maintained when the door is closed. It is to be noted that various kinds of sensors which detect a pressure, a temperature, humidity, and carbon dioxide concentration inside the chamber as well as nitrogen gas concentration or the like as required are provided in the culture chamber 20 (all of them are not shown).

An air supply device 21 configured to adjust an air pressure in the culture chamber 20 is provided on an upper wall portion 20b of the culture chamber 20 (an exhaust device will be described later). The air supply drive 21 is formed of an air supply tube 21a, an electromagnetic valve 21b provided in a line of this tube, a disk filter 21c, and an air supply fan (not shown), and necessarily supplies the air outside the culture chamber 20 into the culture chamber 20 to maintain a higher air pressure in the culture chamber 20 than that in the external environment.

The inside of the culture chamber 20 is divided into a front space 22 and a rear space 23 by a rectifying plate (which will be described later) provided in the circulation device 30. The front space 22 of the culture chamber 20 is a culture compartment and divided into four vertical tiers of space by four horizontally installed shelf boards 22a (see FIG. 1). 12 petri dishes S filled with a culture fluid to culture cells are placed on an upper surface of each shelf board 22a in accordance with each tier (see FIG. 2). It is to be noted that the four shelf boards 22a can be loaded or unloaded through the insulated door 20a as an integral sliding shelf stand.

The circulation device 30 includes a circulation fan 31 which circulates the air in the culture chamber 20, a circulation path 32 (32a to 32f) through which the air in the culture chamber 20 circulates by an operation of the circulation fan 31, a HEPA filter 33 provided in this circulation path 32 (between 32e and 32f), and a rectifying plate 34 which rectifies the air supplied to the inside of the culture chamber 20.

The circulation fan 31 is provided to communicate with the circulation path 32 (between the 32a and 32b), and the air in the culture chamber 20 circulates by an operation of this circulation fan 31. It is to be noted that a type of the circulation fan 31 is not restricted in particular, and any circulation fan which has uniform wind force can suffice.

The circulation path 32 is provided below the culture chamber 20 (in the base 10) and behind the culture chamber 20 (see FIG. 1). The air sucked by the circulation fan 31 flows into the circulation path 32a from a suction port 35 which is opened in a lower wall portion 20c (a part close to the insulated door 20a of the front space 22) of the culture chamber 20, and the air which has flowed into the circulation path 32f from a connecting portion 32g for the circulation path 32e and the circulation path 32f through the circulation paths 32b to 32e is discharged into the rear space 23 of the culture chamber 20 from a discharge port 36 which is opened in a rear wall portion 20d of the culture chamber 20 through the circulation path 32f.

The HEPA filter 33 is provided to communicate with the circulation path 32 (between 32e and 32f), and not only does it clean the air circulating in the circulation path but uniforms the air to be supplied into the culture chamber 20. It is to be noted that a ULPA filter or the like may be adopted in place of this HEPA filter 33. The air discharged into the rear space 23 of the culture chamber 20 through the circulation path 32 as described above is supplied to the front space 22 (the culture compartment) of the culture chamber 20 through the rectifying plate 34.

As described above, the rectifying plate 34 divides the inside of the culture chamber 20 into the front space 22 (the culture compartment) and the rear space 23 (see FIG. 1 and FIG. 2). Further, the air discharged into the rear space 23 through the circulation path 32 is supplied into the front space 22 (the culture compartment) through the rectifying plate 34. A configuration of the rectifying plate 34 is not restricted in particular, and any configuration which rectifies a flow of the air to be supplied into the culture chamber 20 can suffice. It is to be noted that, in this embodiment, the rectifying plate 34 is constituted of a rectangular frame body made of a stainless-steel metal, one porous sheet which covers one surface (a surface on the rear space 23 side) of this frame body, and one slit plate which covers the other surface (a surface on the culture compartment side) of the frame body (all of them are not shown).

A plurality of slits which communicate with front and rear sides are provided in the split plate in parallel with the horizontal direction. The air supplied from the rear space 23 side to the front space 22 (the culture compartment) side forms air of a unidirectional flow (which is a so-called laminar flow) which flows in the inner space of the culture chamber 20 along the horizontal direction by a rectifying function of the rectifying plate 34. Specifically, the air discharged into the rear space 23 is first rectified through the porous sheet. This rectified air is further rectified through the slit plate and flows out into the inner space of the culture chamber 20 from each slit as a unidirectional flow. It is to be noted that particulars of a configuration of the rectifying plate is given in an earlier application (Japanese Patent Application No. 2015-206854) of the present inventors.

Further, in this embodiment, an exhaust device 37 is provided to the circulation path 32b behind the circulation fan 31 in the circulation path 32. The exhaust device 37 is constituted of an exhaust tube 37a, an electromagnetic valve 37b provided in a line of this tube, a disk filter 37c, and an exhaust fan (not shown), and exhausts the air in the culture chamber 20 to the outside of the culture chamber 20 as required. This exhaust device 37 operates to stably maintain an air pressure in the culture chamber 20 higher than that of the external environment in cooperation with the above-described air supply device 21 under control of a microcomputer (not shown) linked with the above-described pressure sensor (not shown). It is to be noted that, in this embodiment, supply/exhaust and aeration of a decontamination gas for decontamination in the culture chamber 20 can be performed through the above-described air supply device 21 and the exhaust device 37.

The temperature regulating device 40 operates to stably maintain a temperature condition (culture conditions) in the culture chamber 20. Although a configuration of the temperature regulating device 40 is not restricted in particular, a temperature regulator formed of a Peltier element is adopted in this embodiment. It is to be noted that, in this embodiment, this temperature regulating device 40 is provided on the circulation path 32 (between 32d and 32e). Since controlling an amount of a current to be supplied to the Peltier element and changing a polarity of the current to be supplied under control of the microcomputer (not shown) linked with the above-described temperature sensor (not shown) can increase or decrease a temperature, a set temperature (37° C. in this embodiment) can be highly accurately maintained. It is to be noted that an electric heater such as a rod-like sheathed heater may be adopted in the circulation path or the culture chamber without using the Peltier element for the temperature regulating device.

The humidifying device 50 operates to stably maintain a humidity condition (the culture conditions) in the culture chamber 20. It is important to stably maintain the temperature condition and the humidity condition in the culture conditions for the culture chamber 20, and a high humidity state which is relative humidity of 95 to 100% RH must be maintained as the humidity condition in particular. In such a high humidity state, condensation occurs due to a slight change in temperature. To avoid this, the air supply device 21, the exhaust device 37, the temperature regulating device 40, and the humidifying device 50 described above operate to stably maintain a temperature and humidity in the culture chamber 20 in cooperation with each other under control of the microcomputer (not shown) linked with the pressure sensor, the temperature sensor, and the humidity sensor mentioned above (all of them are not shown).

Figure 3:
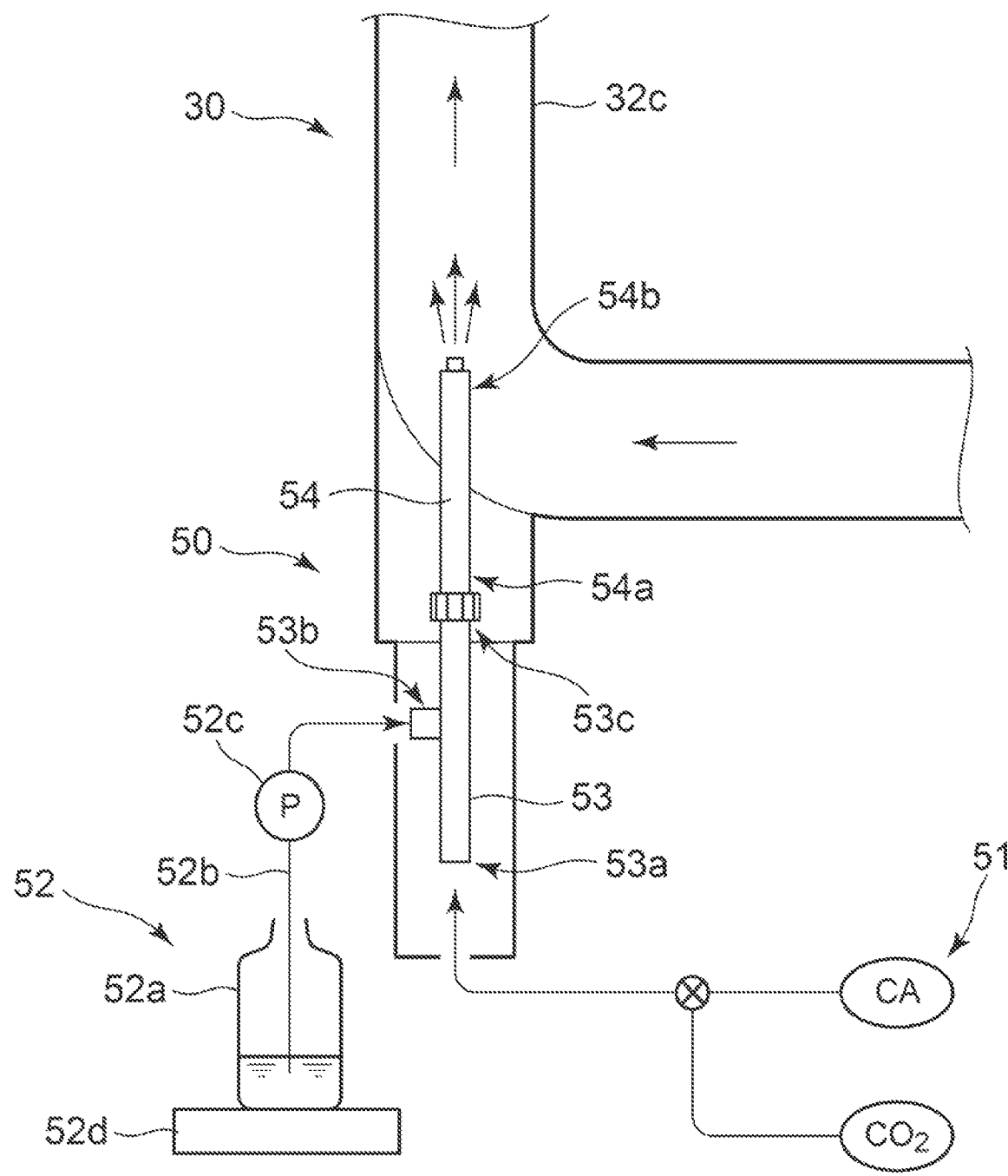
FIG. 3 is a cross-sectional view showing a humidifying device provided in the incubator shown in FIG. 1.

Thus, in this embodiment, a specific humidifying mechanism which can supply an extremely small amount of water vapor into the culture chamber 20 is adopted. The humidifying device 50 is provided on the circulation path 32 (a position of 32c), and supplies the water vapor for humidification to the air circulating in the circulation path 32. FIG. 3 is a cross-sectional view showing the humidifying device included in the incubator according to this embodiment. The humidifying device 50 is constituted of a compressed gas generating device 51, a water supply device 52, a mixed gas-liquid regulator 53, and a vaporizer 54.

As the compressed gas generating device 51, a compressor which generates compressed air is adopted. It is to be noted that, to adjust carbon dioxide concentration, nitrogen gas concentration, or the like in the culture chamber, these gases may be mixed in the compressed air. In FIG. 3, carbon dioxide $CO_2$ is basically mixed in the compressed air CA as required and a mixture is supplied.

The water supply device 52 is constituted of a water storage tank 52a, a water supply piping 52b, a water supply pump 52c, and a load cell 52d. Clean water is stored in the water storage tank 52a, and the tank is mounted on an upper surface of the load cell 52d. One end portion of the water supply piping 52b is immersed in the water in the water storage tank 52a, and the other end portion of the same is connected to the mixed gas-liquid regulator 53. Further, the water supply pump 52c is continuously connected to a line of the water supply piping 52b.

Although a configuration of the water supply pump 52c is not restricted in particular, a water supply pump which can supply a small amount of water in correspondence with a slight change of the humidity sensor is preferred. For example, adopting a volumetric pump or the like is preferred. It is to be noted that, in this embodiment, a peristatic pump which is a kind of volumetric pump is adopted as the water supply pump 52c. Furthermore, in this embodiment, an amount of the water supplied by the water supply pump 52c is not restricted in particular, but it is desirable for the amount to fall within the range of, e.g., 1 g/hr. to 60 g/hr. is preferred. Controlling a small water supply amount enables smoothing a fluctuation range of the humidity in the culture chamber 20. It is to be noted that a supply amount of the water can be detected by the volumetric pump and also detected by the load cell 52d.

The mixed gas-liquid regulator 53 mixes the water supplied from the water supply device 52 with the compressed air supplied from the compressed gas generating device 51 to produce an atomized mixed gas-liquid (mist). It is to be noted that, in this embodiment, an ejector is adopted as the mixed gas-liquid regulator 53. In FIG. 3, the compressed air is supplied from the compressed gas generating device 51 to a driving gas section 53a of the mixed gas-liquid regulator 53. Furthermore, the water is supplied from the water supply device 52 to a sucking section 53b of the mixed gas-liquid regulator 53. On the other hand, a discharge section 53c of the mixed gas-liquid regulator 53 is continuously connected to the vaporizer 54, and the atomized mixed gas-liquid (the mist) is supplied from this section to the vaporizer 54.

The vaporizer 54 vaporizes the atomized mixed gas-liquid (the mist) supplied from the mixed gas-liquid regulator 53 to generate the water vapor. In FIG. 3, one end portion 54a of the vaporizer 54 is continuously connected to the discharge section 53c of the mixed gas-liquid regulator 53. Moreover, the other end portion 54b of the vaporizer 54 is inserted into the circulation path 32c, and the water vapor for humidification is supplied from this other end portion 54b to the air circulating through the circulation path 32.

Figure 4:
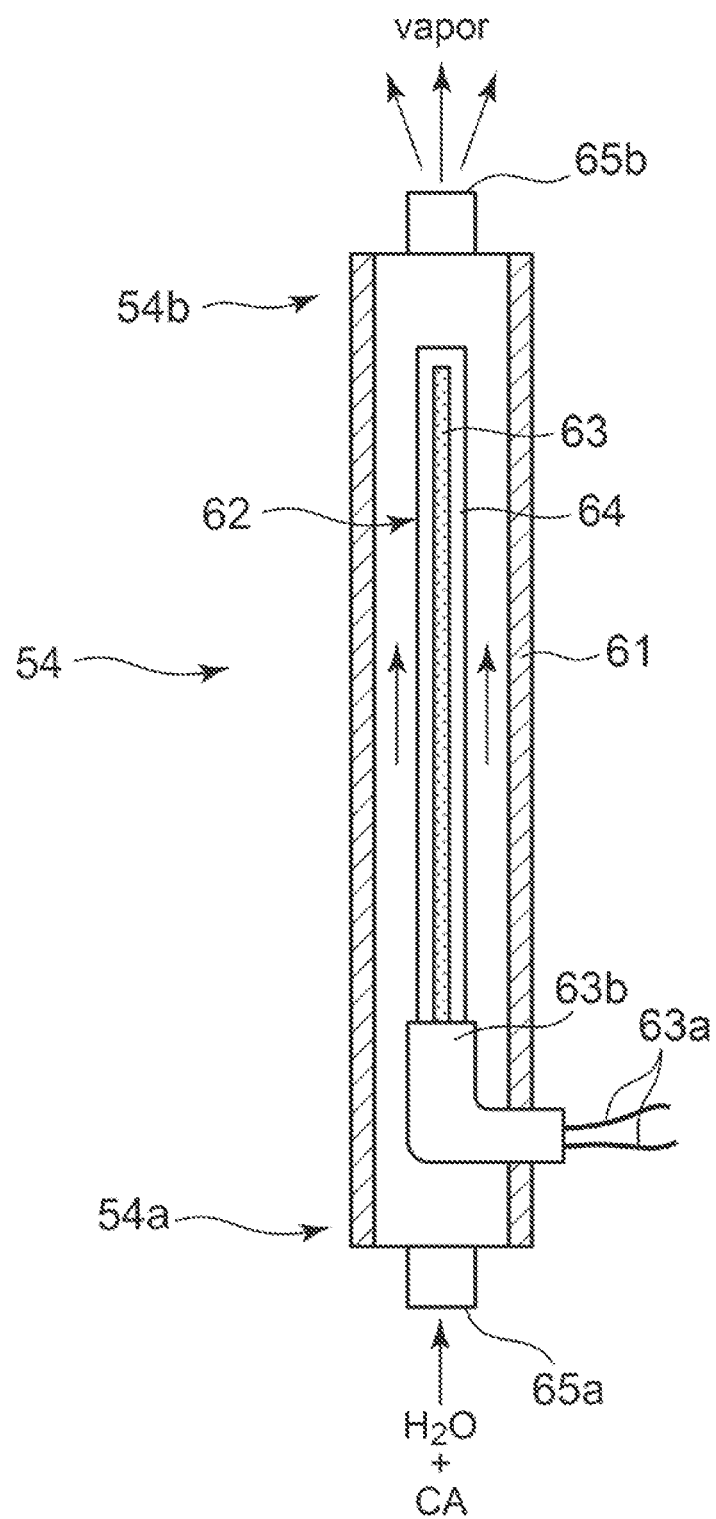
FIG. 4 is a cross-sectional view showing an embodiment of a vaporizer included in the humidifying device shown in FIG. 3.

A description will now be given as to a configuration of the vaporizer 54 adopted in this embodiment. FIG. 4 is a cross-sectional view showing an embodiment of the vaporizer included in the humidifying device. In FIG. 4, the vaporizer 54 is constituted of an outer cylindrical tube 61 having a cylindrical shape extending from the one end portion 54a to the other end portion 54b and a heating element 62 incorporated in this tube in parallel with the longitudinal direction of the outer cylindrical tube 61. The outer cylindrical tube 61 is formed of a stainless-steel cylindrical tube. The heating element 62 includes a heater 63 which extends in parallel with the longitudinal direction of the outer cylindrical tube 61. It is to be noted that a gap through which the mixed gas-liquid (the mist) passes is provided between an inner peripheral surface of the outer cylindrical tube 61 and the heating element 62.

The heater 63 is installed at one outer peripheral end portion (the one end portion 54a side of the vaporizer 54) of the outer cylindrical tube 61 with the use of a connecting terminal 63b made of silicon rubber, and generates heat upon receiving electric power from electric wires 63a. It is to be noted with a surface of the heater 63 which is heated to a high temperature is coated with quartz glass 64. Additionally, in this embodiment, the inner peripheral surface of the outer cylindrical tube 61 is also coated with the quartz glass. It is to be noted that a configuration of the heater 63 is not restricted in particular, and it may be a rod-shaped heater or may be a coil-shaped heater. Further, coating the surface of the heater and the inner peripheral surface of the outer cylindrical tube with the quartz glass is not necessarily required, but coating is performed to prevent dust generation and improve heat efficiency in this embodiment.

In such a vaporizer 54, the atomized mixed gas-liquid (the mist) supplied from the mixed gas-liquid regulator 53 is led into the vaporizer 54 from an introducing port 65a which is opened at the one end portion 54a of the vaporizer 54. The mixed gas-liquid (the mist) which has been led into the vaporizer 54 passes through a gap between the outer cylindrical tube 61 and the heating element 62 while being heated by the heating element 62, and moves toward a discharge port 65b which is opened at the other end portion 54b of the vaporizer 54. Meanwhile, water (a liquid) in the mixed gas-liquid is heated and vaporized by the heating element 62 to turn to water vapor (a gas), and discharged from the discharge port 65b. It is to be note that a temperature of the water vapor to be discharged may be controlled while measuring the temperature of the water vapor at the discharge port 65b with the use of a temperature sensor.

Figure 5:
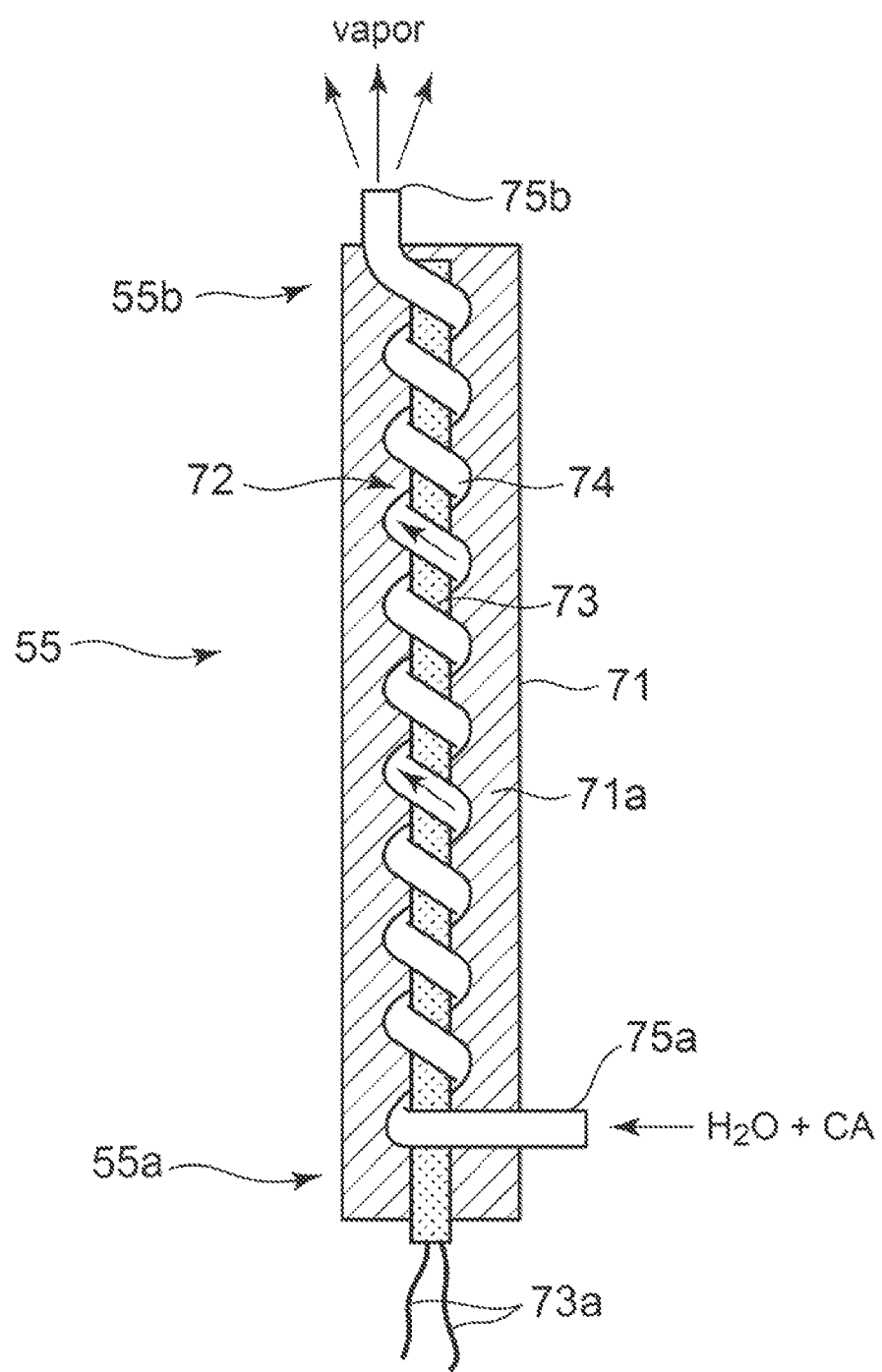
FIG. 5 is a cross-sectional view showing another embodiment of the vaporizer included in the humifying device shown in FIG. 3.

A description will now be given as to another embodiment of the vaporizer. FIG. 5 is a cross-sectional view showing another embodiment of the vaporizer included in the humidifying device. In FIG. 5, a vaporizer 55 is constituted of an outer cylindrical tube 71 having a cylindrical shape extending from one end portion 55a to the other end portion 55b and a heating element 72 incorporated in the outer cylindrical tube 71 in parallel with a longitudinal direction thereof. The outer cylindrical tube 71 is formed of a stainless-steel cylinder and has a heat insulating material 71a filled therein. The heating element 72 includes a rod-like cartridge heater 73 extending parallel to the longitudinal direction of the outer cylindrical tube 71 and an evaporator tube 74 spirally wound around an outer peripheral of the cartridge heater 73 along the longitudinal direction. It is to be noted that the cartridge heater 73 and the evaporator tube 74 are coated with the heat insulating material 71a. The cartridge heater 73 is installed at one end portion (the one end portion 55a side of the vaporizer 55) of the outer cylindrical tube 71, and generates heat upon receiving electric power from electric wires 73a.

In such a vaporizer 55, an atomized mixed gas-liquid (mist) supplied from a mixed gas-liquid regulator 53 is led into the evaporator tube 74 from an introducing port 75a of the evaporator tube 74 which is opened in an outer periphery of the one end portion 55a of the vaporizer 55. The mixed gas-liquid (the mist) led into the evaporator tube 74 passes through the evaporator tube 74 while being heated by the cartridge heater 73 which is contact with the evaporator tube 74, and moves toward a discharge port 75b of the evaporator tube 74 which is opened at the other end portion 55b of the vaporizer 55. Meanwhile, water (a liquid) in the mixed gas-liquid is heated and vaporized by the cartridge heater 73 to turn to water vapor (a gas), and discharged from the discharge port 75b. It is to be noted that a temperature of the water vapor to be discharged may be controlled while measuring the temperature of the water vapor at the discharge port 75b with the use of a temperature sensor.

Adopting the vaporizer 54 or 55 having such a configuration is effective in terms of the heat efficiency to a small amount of water supply falling within the range of, e.g., 1 g/hr. to 60 g/hr. and also enables smoothing a fluctuation range of the humidity in the culture chamber 20. Further, the mixed gas-liquid is heated by the heating element 62 or 72 to turn to the high-temperature water vapor. In this embodiment, to assuredly guarantee an aseptic state of the water vapor, a temperature of the water vapor generated by the vaporizer 54 or 55 is controlled to 100° C. or a higher temperature. Consequently, the water vapor generated by the vaporizer 54 or 55 is sterilized and can be directly supplied into the air circulating in the circulation path 32 without passing through an air filter.

It is to be noted that an amount of the high-temperature water vapor discharged by the vaporizer 54 or 55 is extremely small, and hence a temperature of the air circulating in the circulation path 32 is not greatly changed. Furthermore, in this embodiment, a temperature is constantly regulated (not only temperature rising but also temperature lowering is performed) by the Peltier element of the temperature regulating device 40 provided on the circulation path 32 (see FIG. 1) In this manner, the humidity and temperature environment in the culture chamber 20 may be controlled based on an amount and a temperature of the water vapor discharged by the vaporizer 54 or 55. Thus, in the culture chamber 20 which is airtightly shielded from the external environment and maintains an inner aseptic environment (e.g., the grade A), the grade A aseptic environment is likewise maintained in this embodiment where the water vapor is supplied from the external environment.

A description will now be given as to a flow of the air and a function of the incubator 100 during an operation in the thus-configured incubator 100 according to this embodiment. In FIG. 1, the inside of each of the culture chamber 20 and the regulation path 32 is maintained in an aseptic/dustless state. Moreover, the air supply device 21 and the exhaust device 37 are operated so that an air pressure in the culture chamber 20 is maintained higher than that in the external environment. Consequently, the inside of the culture chamber 20 maintains the grade A conforming to GMP.

Additionally, a temperature in the culture chamber 20 is maintained at 37±0.5° C. The humidity in the culture chamber 20 is maintained at 95% RH or more to avoid a change in an osmotic pressure caused due to evaporation of a culture solution. Further, carbon dioxide concentration (nitrogen gas concentration as required) in the culture chamber 20 is maintained at the concentration which is required to assure conditions optimum for the culture.

In this state, when the circulation fan 31 operates, the air in the front space 22 (the culture compartment) of the culture chamber 20 flows into the circulation path 32 from the suction port 35 which is opened in the lower wall portion 20c (a part close to the insulated door 20a of the front space 22) of the culture chamber 20. The air flowing in the circulation path 32 is subjected to the humidity regulation by the humidifying device 50, the temperature regulation by the temperature regulating device 40, and cleaning and uniformizing by the HEPA filter 33 under control of the microcomputer (not shown) linked with the various kinds of sensors. Then, the air flowing in the circulation path 32 is discharged from the circulation path 32f into the rear space 23 of the culture chamber 20 through the discharge port 36 opened in the rear wall portion 20d of the culture chamber 20. It is to be noted that, in FIG. 1, flows of the air flowing in the circulation path 32 are denoted by arrows.

Here, as described above, the inside of the culture chamber 20 is maintained in the aseptic/dustless state. However, cleaning the air by the HEPA filter 33 in the circulation path 32 enables perfectly assuring the aseptic/dustless state in the culture chamber 20. For example, even if a foreign matter such as a microorganism is mixed in the circulation path 32 by any incident, the aseptic/dustless state in the culture chamber 20 is assured by a function of the HEPA filter 33.

The air discharged into the rear space 23 of the culture chamber 20 is rectified by the rectifying plate 34 and supplied to the front space 22 (the culture compartment) of the culture chamber 20. The air supplied to the front space 22 (the culture compartment) through the rectifying plate 34 forms air of a unidirectional flow (a laminar flow) flowing through the front space 22 (the culture compartment) in the horizontal direction (from the left to the right in FIG. 1 and FIG. 2). It is to be noted that the temperature and the humidity of the air of the unidirectional flow flowing through the front space 22 (the culture compartment) and the carbon dioxide concentration are accurately maintained at the set conditions. It is to be noted that, in FIG. 1 and FIG. 2, flows of the air flowing through the front space 22 (the culture compartment) are denoted by arrows.

In FIG. 1, the air discharged through the rectifying plate 34 flows along the horizontal direction (from the left to the right in FIG. 1) in each of four chambers partitioned by the upper wall portion 20b, the lower wall portion 20c, and the four shelf boards 22a. The temperature, the humidity, and a flow velocity of this air are maintained constant. Furthermore, in each of the four partitioned chambers, the petri dishes S filled with the culture solution are mounted on each shelf board (in this embodiment, 12 petri dishes are mounted on each shelf board). Thus, the air of the unidirectional flow regulated to the fixed temperature, humidity, and carbon dioxide concentration flows on surfaces of the respective petri dishes S (from the left to the right in FIG. 2) at a fixed flow velocity. Further, in the culture chamber 20, the temperature, the humidity, and the carbon dioxide concentration of the air of the unidirectional flow are detected by the temperature sensor, the humidity sensor, and the carbon dioxide concentration sensor described above.

Here, each petri dish S is generally made of glass, and its coefficient of overall heat transmission (a K value) is not small. However, heating based on radiation or stirring performed in conventional incubators requires a very long time to increase a temperature of a culture solution in each petri dish S to the culture conditions. On the other hand, in this embodiment, the air of the unidirectional flow having a fixed temperature is constantly supplied, and supply of a heat quantity to each petri dish S increases. Thus, in this embodiment, an apparent coefficient of overall heat transmission (the K value) of each petri dish S further increases, and a temperature of the culture solution in the petri dish S can be raised to the culture condition in a short time. Thus, in this embodiment, it is possible to provide the incubator which can increase a temperature in each petri dish having an object to be cultured to a predetermined temperature in a short time.

As described thus far, in the present invention, it is possible to provide the incubator which can uniformly maintain the temperature/humidity in the culture chamber without producing dew condensation in the culture chamber. Further, in the present invention, it is possible to provide the incubator which raises the air pressure in the culture chamber higher than that in the external environment to maintain the aseptic environment and prevents the water vapor to be supplied from adversely affecting the inner aseptic environment.

It is to be noted that, to carry out the present invention, there are the following various modifications without being restricted to the foregoing embodiment.

(1) In the foregoing embodiment, the positions of the air supply device, the exhaust device, the temperature regulating device, and the humidifying device are specified as respective predetermined positions, but the culture chamber or the circulation path may be provided at different positions without being restricted thereto.

(2) In the foregoing embodiment, the temperature sensor, the humidity sensor, and the carbon dioxide concentration sensor are placed in the culture chamber, but they may be provided in the circulation path without being restricted thereto.

(3) In the foregoing embodiment, the Peltier element is used as the temperature regulating device for the air, but an electric heater such as a rod-like sheathed heater may be adopted in the circulation path or the culture chamber without being restricted thereto.

(4) In the foregoing embodiment, the four shelf boards are provided in tires in the culture chamber, but there or less or five or more shelf boards may be provided in tiers without being restricted thereto.

(5) In the foregoing embodiment, the carbon dioxide supplying means is provided to regulate the carbon dioxide concentration in the culture chamber, but the carbon dioxide supplying means does not have to be provided depending on the culture conditions without being restricted thereto.

(6) In the foregoing embodiment, the carbon dioxide supplying means is provided to regulate the carbon dioxide concentration in the culture chamber, but the nitrogen gas supplying gas may be provided in addition to the carbon dioxide supplying means or in place of the carbon dioxide supplying means to regulate the nitrogen gas concentration in the culture chamber depending on the culture conditions without being restricted thereto.

(7) In the foregoing embodiment, the rectifying plate formed of one porous sheet and one slit plate is adopted, but one or more porous sheets may be adopted without being restricted thereto. In this case, as the porous sheet, it is preferred to use screen gauze or a porous ceramic plate.

(8) In the foregoing embodiment, the rectifying plate formed of one porous sheet and one slit plate is adopted, but the incubator may be configured with no use of the rectifying plate without being restricted thereto.

REFERENCE SIGNS LIST

100 . . . incubator, 10 . . . base, 20 . . . culture chamber, 20a . . . insulated door, 20b to 20d . . . insulated wall, 21 . . . air supply device, 21a . . . air supply tube, 21b . . . electromagnetic valve, 21c . . . disk filter, 22 . . . front space, 22a . . . shelf board, 23 . . . rear space, 30 . . . circulation device, 31 . . . circulation fan, 32 . . . circulation path, 33 . . . HEPA filter, 34 . . . rectifying plate, 35 . . . suction port, 36 . . . discharge port, 37 . . . exhaust device, 37a . . . air supply tube, 37b . . . electromagnetic valve, 37c . . . disk filter, 40 . . . temperature regulating device, 50 . . . humidifying device, 51 . . . compressed gas generating device, 52 . . . water supply device, 52a . . . water storage tank, 52b . . . water supply tube, 52c . . . water supply pump, 52d . . . load cell, 53 . . . mixed gas-liquid regulator, 54 . . . vaporizer, 61 and 71 . . . outer cylindrical tube, 62 and 72 . . . heating element, 63 and 73 . . . heater, 64 . . . quartz glass, 74 . . . evaporator tube, and S . . . petri dish.

The invention claimed is:

1. An incubator comprising:
a culture chamber that comprises an insulated door and insulated walls;
a circulation device configured to circulate air in the culture chamber;
a temperature regulating device configured to regulate a temperature of the air in the culture chamber; and
a humidifying device configured to humidify the air in the culture chamber,
wherein the humidifying device comprises:
a compressed gas generating device configured to generate a compressed gas;
a water supply device configured to supply water to the circulation device;
a mixed gas-liquid regulator fluidly connecting each of the compressed gas generating device and the water supply device to the circulation device and configured to mix gas delivered by the compressed gas generating device and water delivered by the water supply device to form a mist containing a mixture of said gas with said water; and
a vaporizer configured between the mixed gas-liquid regulator and the circulation device to receive and vaporize said mist to produce water vapor that is sterilized and to directly supply said sterilized water vapor to the air circulated by the circulation device without passing said water vapor through an air filter,
wherein:
the vaporizer comprises an outer cylindrical tube having a cylindrical shape and a heating element extended in the outer cylindrical tube in parallel with a longitudinal direction thereof,
the heating element comprises a rod-like heater oriented along said longitudinal direction and an evaporator tube spirally wound around an outer periphery of the heating element.

2. An incubator comprising:
a culture chamber that comprises an insulated door and insulated walls;
a circulation device configured to circulate air in the culture chamber;
a temperature regulating device configured to regulate a temperature of the air in the culture chamber; and
a humidifying device configured to humidify the air in the culture chamber;
wherein the humidifying device comprises:
a compressed gas generating device configured to generate a compressed gas;
a water supply device configured to supply water to the circulation device;
a mixed gas-liquid regulator fluidly connecting each of the compressed gas generating device and the water supply device to the circulation device and configured to mix gas delivered by the compressed gas generating device and water delivered by the water supply device to form a mist containing a mixture of said gas with said water; and
a vaporizer that comprises an outer cylindrical tube and a heating element extended in the outer cylindrical tube in parallel with a longitudinal direction thereof, the vaporizer configured between the mixed gas-liquid regulator and the circulation device to receive said mist and pass said mist through a space between the heating element and the outer cylindrical tube to produce a sterilized water vapor, and to directly supply said sterilized water vapor to the air circulated by the circulation device without passing said water vapor through an air filter.

3. The incubator according to claim 2, wherein the heating element has a heater coated with quartz glass.

4. The incubator according to claim 1 or 2, comprising:
an air supply device in fluid communication with the culture chamber at a point of discharge of air from the circulation device into the culture chamber, and
an exhaust device disposed in a circulation path of the circulation device downstream from the culture chamber,
said air supply device and said exhaust device aggregately configured to maintain air pressure that is higher in the incubator than in environment external to said incubator.

5. The incubator according to claim 1 or 2, wherein the circulation device comprises:
a circulation path comprising a circulation fan configured to supply the air sucked from one end portion of the culture chamber into the culture chamber through the other end portion of the culture chamber; and
a rectifying member configured to rectify the air supplied into the culture chamber through the circulation path such as to form a substantially unidirectional flow of air, in the culture chamber, directed along shelves of the culture chamber.

6. The incubator according to claim 1 or 2, wherein the gas delivered by the compressed gas generating device is a mixed gas containing one or more of air, carbon dioxide, and nitrogen.

7. The incubator according to claim 1 or 2, wherein the vaporizer is configured to discharge a supply amount of said water vapor within the range from 1 g/hr to 60 g/hr.

* * * * *